United States Patent
Wallace

(10) Patent No.: US 10,881,775 B2
(45) Date of Patent: Jan. 5, 2021

(54) DIALYSIS MACHINE AND ULTRAFILTRATION

(71) Applicant: QUANTA DIALYSIS TECHNOLOGIES, LTD., Warwickshire (GB)

(72) Inventor: Mark Wallace, Warwickshire (GB)

(73) Assignee: QUANTA DIALYSIS TECHNOLOGIES LTD., Warwick (GB)

(*) Notice: Subject to any disclaimer, the term of this patent is extended or adjusted under 35 U.S.C. 154(b) by 246 days.

(21) Appl. No.: 15/771,366

(22) PCT Filed: Oct. 27, 2016

(86) PCT No.: PCT/GB2016/053339
§ 371 (c)(1),
(2) Date: Apr. 27, 2018

(87) PCT Pub. No.: WO2017/072511
PCT Pub. Date: May 4, 2017

(65) Prior Publication Data
US 2018/0344915 A1    Dec. 6, 2018

(30) Foreign Application Priority Data

Oct. 28, 2015   (GB) .................................. 1519084.6

(51) Int. Cl.
*A61M 1/16* (2006.01)
*A61M 1/26* (2006.01)
*A61M 1/34* (2006.01)

(52) U.S. Cl.
CPC ............ *A61M 1/1647* (2014.02); *A61M 1/16* (2013.01); *A61M 1/1637* (2014.02);
(Continued)

(58) Field of Classification Search
CPC .... A61M 1/16; A61M 1/1601; A61M 1/1637; A61M 1/1647; A61M 1/1649;
(Continued)

(56) References Cited

U.S. PATENT DOCUMENTS 3,774,762 A   11/1973   Lichtenstein
4,161,264 A   7/1979    Malmgren
(Continued)

FOREIGN PATENT DOCUMENTS

DE   10024447 A1   11/2001
EP   0165751 A2   12/1985
(Continued)

OTHER PUBLICATIONS

International Search Report and Written Opinion for International Application No. PCT/GB2016/053339, dated Jan. 3, 2017.
(Continued)

*Primary Examiner* — John Kim
(74) *Attorney, Agent, or Firm* — Cooley LLP

(57) ABSTRACT

The invention relates to a dialysis machine capable of performing ultrafiltration without the need for a dedicated ultrafiltration pump. The system uses a pair of membrane flow balance pumps wherein the operation and/or the volume flow rate of the pumps can be modified during operation to bring about a net movement of dialysate either into or from the dialyser. The direction of flow of the dialysate in the dialyzer is reversible and the dialyzer can comprise two dialysate inlets, one at each end, and two dialysate outlets, one at each end.

15 Claims, 4 Drawing Sheets

(52) U.S. Cl.
CPC .......... *A61M 1/1649* (2014.02); *A61M 1/267* (2014.02); *A61M 1/341* (2014.02); *A61M 2205/12* (2013.01); *A61M 2205/128* (2013.01)

(58) Field of Classification Search
CPC .. A61M 1/267; A61M 1/341; A61M 2205/12; A61M 2205/128
See application file for complete search history.

(56) References Cited

U.S. PATENT DOCUMENTS

| | | | |
|---|---|---|---|
| 4,969,991 | A | 11/1990 | Valadez |
| 5,032,265 | A | 7/1991 | Jha et al. |
| 5,252,213 | A | 10/1993 | Ahmad et al. |
| 5,421,823 | A | 6/1995 | Kamen et al. |
| 5,643,201 | A | 7/1997 | Peabody et al. |
| 5,658,456 | A | 8/1997 | Kenley et al. |
| 6,251,279 | B1 | 6/2001 | Peterson et al. |
| 7,648,627 | B2 | 1/2010 | Beden et al. |
| 8,535,525 | B2 | 9/2013 | Heyes et al. |
| 8,685,244 | B2 | 4/2014 | Heyes et al. |
| 9,744,285 | B2 | 8/2017 | Heyes et al. |
| 2004/0195157 | A1 | 10/2004 | Mullins et al. |
| 2004/0206703 | A1 | 10/2004 | Bosetto et al. |
| 2005/0020961 | A1 | 1/2005 | Burbank et al. |
| 2009/0211975 | A1 | 8/2009 | Brugger et al. |
| 2009/0230043 | A1 | 9/2009 | Heyes et al. |
| 2010/0089807 | A1 | 4/2010 | Heyes et al. |
| 2011/0132838 | A1 | 6/2011 | Curtis et al. |
| 2014/0251885 | A1 | 9/2014 | Heyes |
| 2017/0252498 | A1 | 9/2017 | Heyes et al. |
| 2018/0133391 | A1 | 5/2018 | Heyes et al. |
| 2018/0154059 | A1 | 6/2018 | Heyes et al. |

FOREIGN PATENT DOCUMENTS

| | | |
|---|---|---|
| WO | 198101800 A1 | 7/1981 |
| WO | 2000006217 A1 | 2/2000 |
| WO | WO 2003/101510 | 12/2003 |
| WO | WO 2006/120415 | 11/2006 |
| WO | WO 2006/120417 | 11/2006 |
| WO | 2013110919 A1 | 8/2013 |
| WO | 20130110906 A1 | 8/2013 |
| WO | 20130114063 A1 | 8/2013 |
| WO | 2015007596 A1 | 1/2015 |

OTHER PUBLICATIONS

International Search Report and Written Opinion for International Application No. PCT/GB2006/001671, dated Nov. 24, 2006, 13 pages.
International Search Report and Written Opinion for International Application No. PCT/GB2006/001668, dated Sep. 5, 2006, 8 pages.
International Preliminary Report on Patentability for International Application No. PCT/GB2006/001668, dated Nov. 6, 2007, 6 pages.
Office Action for Australian Application No. 2012244377, dated Mar. 14, 2013, 3 pages.
Office Action for European Application No. 06727035.5, dated Feb. 15, 2013, 4 pages.

DIALYSIS MACHINE AND ULTRAFILTRATION

This application is a National Stage Entry entitled to and hereby claiming priority under 35 U.S.C. §§ 365 and 371 to corresponding PCT Application No. PCT/GB2016/053339, filed Oct. 27, 2016, entitled "Dialysis Machine And Ultrafiltration", which in turn claims priority to G.B. Patent Application No.: 1519084.6, filed Oct. 28, 2015, entitled the same. The disclosures of the above applications are incorporated herein by reference in their entireties.

FIELD OF INVENTION

The invention relates to a dialysis machine suitable for performing ultrafiltration. In particular, the invention relates to a dialysis machine where ultrafiltration can be carried out without the need for a specific ultrafiltration pump.

BACKGROUND OF INVENTION

Dialysis is a treatment which replaces the renal function of removing excess fluid and waste products (e.g. potassium) from the blood. The treatment is either employed where renal function has deteriorated to an extent that uremic syndrome becomes a threat to the body's physiology (acute renal failure) or when a long standing renal condition impairs the performance of the kidneys (chronic renal failure). During most dialysis treatments, it is often the case that excess fluid will be generated by the patient and will interfere with the volumetrically controlled quantities of dialysate passing through the dialyser of the dialysis machine. Conventionally, this excess fluid is removed using an ultrafiltration pump. The ultrafiltration pump is activated sometimes continuously, sometimes intermittently to deal with any excess build-up of fluid.

However, the presence of a specific pump for ultrafiltration and accompanying tubing, in addition to the dialysate and blood pumps already required by the dialysis machine, complicates the manufacture, maintenance, miniaturisation and operation of dialysis machines.

Accordingly, it is desirable to provide an alternative means of carrying out ultrafiltration which does not include complex modification of the dialysate delivery and removal circuits. The present invention is intended to overcome or at least ameliorate some of the above described problems.

SUMMARY OF INVENTION

There is provided in the first aspect of the invention a dialysis machine for ultrafiltration comprising a dialyser, a first pump and a second pump, wherein the pumps are each adapted to deliver a fresh dialysate solution to the dialyser and remove a spent dialysate solution from the dialyser, wherein the volume flow rates of the pumps are different, and characterised in that the operation of said pumps is configured to remove excess fluid from the dialyser and/or deliver excess fluid to the dialyser.

The inventors of the present invention have realised that it is possible to achieve ultrafiltration using only two pump systems wherein the volume flow rates of these pumps are different and wherein the operation of these pumps is alternated so that an uneven number of pump cycles occurs in one "pumping direction" versus another pumping direction. This allows for the gradual delivery and/or removal of excess fluid to/from the dialyser.

The pumps each have a pump chamber defining a pump volume. In one arrangement, the volumes of the pump chambers are different. In another arrangement, the volumes are the same but the pumps are operated at different pump frequencies to achieve differential volume flow rates.

This is particularly advantageous as this system does not require a separate, dedicated ultrafiltration pump in order to perform ultrafiltration. The amount of fluid to be delivered to or taken away from the dialyser can be customised purely by varying the number of pump cycles in a particular flow direction.

The term "pump" as used herein, unless otherwise stated, is not intended to cover just the pump chamber alone. It is also intended to refer to the accompanying tubing, valves and other apparatus associated with the pump that also carry fluid. For instance, in the present invention, the pump is adapted for sending dialysate solution to the dialyser and preferably includes: tubing delivering dialysate to the pump chamber from a dialysate source; a pump chamber; and tubing to carry dialysate exiting the pump chamber. Both these tubing portions are preferably equipped with valves (preferably membrane valves).

The term "flow direction" is intended to refer to the way in which the first and second pumps are configured. For instance, when the first pump is the pump responsible for delivering fresh dialysate solution to the dialyser and the second pump is responsible for removing spent dialysate solution from the dialyser, the dialysate travels through the system in a first flow direction. Alternatively, when the second pump is responsible for delivering fresh dialysate solution to the dialyser and the first pump is responsible for removing spent dialysate solution from the dialyser, the dialysate flows in a second flow direction.

The term "fresh dialysate solution" is intended to mean a dialysate solution which has not already been passed through a dialyser. The term "spent dialysate solution" is intended to refer to dialysate solution which has already passed through a dialyser and typically contains compounds extracted from blood as the dialysate solution passed through the dialyser.

It is typically the case that the dialysis machine of the invention is a volumetrically controlled system. The term "excess fluid" is intended to refer to the net movement of fluid to and/or from the dialyser. For instance, in the situation where the first pump is delivering a dialysate solution to the dialyser and the second pump is removing spent dialysate from the dialyser and the volume of dialysate delivered/received by actuation of the first and second pumps is 20 ml and 30 ml respectively, the excess fluid would be 10 ml drawn from the dialyser by the second pump. In use, the source of this excess fluid typically comes from the blood of the patient as it passes through the dialyser.

In one embodiment of the invention, it is the case that the volumes of the first pump and second pump do not change. This is advantageous as excess fluid can be delivered and/or removed from the dialyser purely by alternating the flow direction for a given number of pumping cycles. There is no need to modify the volume of the pumps in order to change the net movement of fluid. This reduces the need for extra moving parts and hence reduces maintenance requirements and manufacturing costs.

Alternatively, it may be the case that the volume of at least one of the pumps is variable. This is advantageous as the amount of excess fluid per pumping cycle can be customised by changing the size of the pump chambers or other elements of the pump (for example, the volume of the valves or tubing). It is often the case that both of the pumps present in the invention will have variable volumes however, a device where only one of the pumps has a variable volume is also envisaged.

Typically, it is the case that the operation of said pump is configured to remove excess fluid from the dialyser. Typically during a dialysis treatment, excess fluid is generated by the patient and it is desirable to have this excess fluid removed. However, there are situations where it is desirable to deliver excess fluid to the dialyser. For example, it can be difficult to remove large blood impurities (such as proteins) from the blood. Therefore, by delivering excess fluid to the dialyser (and in turn to the patient), excess fluid can subsequently be drawn from the dialyser causing solute drag to help remove large blood impurities from the blood whilst retaining an net overall movement of fluid. Having a system where both pumps have variable volumes and where both pumps are capable of delivering fresh dialysate to the dialyser and removing spent dialysate from the dialyser is advantageous as the device can perform dialysis and ultrafiltration in either flow direction. This is useful for a number of reasons, including providing an alternative pumping mode in the event that problems occur with one of the two pumping mode.

There is also provided, in a second aspect of the invention, a dialysis machine for ultrafiltration comprising a dialyser; a first pump and a second pump, wherein the first pump is adapted to deliver fresh dialysate solution to the dialyser and the second pump is adapted to remove spent dialysate solution from the dialyser; wherein the volume flow rate of at least one of the pumps is variable; characterised in that the volumes flow rate of the pumps is configurable to remove excess fluid from the dialyser and/or deliver excess fluid to the dialyser.

This is advantageous as it allows ultrafiltration to be performed even in systems only capable of pumping in a single flow direction.

In one embodiment, the pumps have chambers and the volume of at least one of the pump chambers may be variable. Excess fluid can be delivered to the dialyser or removed from the dialyser by varying the volume of the pump chambers without needing to modify the flow direction. This system can be used in dialysis machines where it is not possible to modify the operations of the first and second pumps such as, where the flow direction cannot be changed.

It is typically the case that the initial volume of the pump chambers will have volumes equal to each other but wherein the volume of at least one of the pump chambers is variable. The mechanism by which the volume of the pumps is varied is not particularly limited and depends to a large extent on the type of pump used in the machine.

It is typically the case that the pump chambers may have variable volumes and one or both of the pumps can be switched between two configurations each having a different volume. Typically, the first configuration is such that the volume of both pump chambers in the system are equal, and the second configuration is such that the pump chamber of the first pump is either greater than or less than the volume of the pump chamber of the second pump in the system. Accordingly, in use, the pump having variable volume can be switched between the configurations in order to modify the amount of excess fluid either delivered to or removed from the dialyser.

The mechanism by which the pump chamber volume is varied is not particularly limited but may, for example, be done by providing one or more deployable protrusions which decrease the volume of the pump chamber.

Alternatively, other sections of the system can be varied to bring about the difference in volume of the pumps. For instance, in one embodiment, the dialysis machine may comprise at least one valve and it is typically the case that the valve is a membrane valve. Membrane valves are described in detail in WO 2013/110919 on pages 14 and 15, the contents of which are expressly incorporated herein. The valves are actuated by application of pneumatic pressure. In this embodiment, the dialysis machine is configured to vary the volume of the valve by controlling the pressure differential across the membrane of the membrane valve in order to change the shape of the membrane when the membrane valve is in a closed configuration.

Dictating the shape of the membrane by controlling the pressure differential across the membrane allows the volume of the valve to be controlled. This embodiment is advantageous as it makes use of the membrane covering the valves to bring about a physical change in the volume of the system. This volume difference can be customised by varying the pressure applied to the membrane, taking account of pressure within the system, to provide the required membrane shape.

Typically, the dialysis machine comprises one or more pressure sensors that enable the dialysis machine to better calculate the pressure differential across the membrane. Back pressure can build and vary in a dialysis system depending on how the valves, pumps and the dialyser are operated. Pressure differences can also be caused as a result of changes in patient blood pressure during treatment. When these parameters are taken into account an improved control of the pressure differential across the membrane is achieved.

As an alternative to varying the physical volume of the pump chambers, one embodiment of the invention involves a dialysis machine for ultrafiltration comprising: a dialyser; a first pump and a second pump, wherein the first pump is adapted to deliver a fresh dialysate solution to the dialyser and the second pump is adapted to remove a spent dialysate solution from the dialyser; wherein the pumps have pump chambers of substantially equal volume and wherein one of the pumps is configured to be operated at a different frequency than the other pump to remove excess fluid from the dialyser and/or deliver excess fluid to the dialyser.

In this embodiment, there is no requirement for the pump chambers to have different volumes. The pumps can be operated an uneven number of times in order to deliver excess fluid to the dialyser or remove excess fluid from the dialyser. This is advantageous as existing systems equipped with pump chambers of equal, invariable volumes can be retrofitted to provide ultrafiltration without the need for a dedicated ultrafiltration pump.

It is often the case in the above embodiments that both the first and second pumps are adapted to deliver fresh dialysate solution to the dialyser and remove spent dialysate solution from the dialyser. However, this is not essential. It is advantageous for the role of the first and second pumps to be able to be swapped as this compensates for small differences in the volume of the pump chambers that result from the manufacturing process.

As with the first aspect of the invention, it is typically the case in the second aspect of the invention that the operation of said pumps is configured to remove excess fluid from the dialyser. Typically, during dialysis, excess fluid is generated by the patient and this fluid ideally needs to be removed. It is typically the case that the volume of only one pump chamber is variable. This reduces the complexity of the system e.g. limiting the number of moving parts. However, it is possible that both pumps may pump a variable volume of dialysate.

The pumps that are used in the aspects of the invention described above are typically flow balance pumps. Further, it is typically the case that flow balance pumps are membrane pumps, each pump comprising a cavity covered by a flexible membrane.

The base of the pump cavity may comprise one or more deployable protrusions where the volume of the pump chamber is variable. These deployable protrusions are advantageous when used with membrane pumps because when the flexible membrane is drawn towards the base of the pump cavity through the manipulation of a pressure differential across the membrane (typically done by pneumatic means), the film abuts against these protrusions rather than lying flush against the base of the pump cavity, thereby reducing the total volume of the pump chamber.

It is typically the case that the difference in the volume flow rate of the first and second pumps in the aspects of the invention described above is at least 1%. It is preferred in dialysate treatment to gradually remove fluid from a patient rather than remove fluid from a patient quickly as such more rapid removal of fluid can be unpleasant to a user. Accordingly, small differences in volume of dialysate pumped by the pumps size are preferred. Typically, the difference in volume flow rate of the first and second pumps is in the range of 5% to 50%.

During a typical dialysis treatment, the rate of fluid removal from a patient may vary from 0.0 L to 2.0 L per hour. More typically, the rate of fluid removal varies from 0.0 L to 1.0 L per hour.

It is typically the case that the dialysis machine of the present invention does not comprise a separate ultrafiltration pump. Although it is preferred with the present invention to avoid making use of a separate ultrafiltration pump (for the reasons outlined above) an additional ultrafiltration pump may be included in the dialysis machine of the present invention, for instance, as a backup in case of certain system malfunctions or in order to augment the ultrafiltration process which can be performed using the device as described above.

There is also provided in a third aspect of the invention a method of operating the dialysis machine according to the first aspect of the invention comprising the steps of: delivering fresh dialysate solution to the dialyser using the first pump and removing spent dialysate solution from the dialyser using the second pump for a first number of pump cycles; delivering fresh dialysate solution to the dialyser using the second pump and removing spent dialysate solution from the dialyser using the first pump for second number of cycles; characterised in that the first number of pump cycles is different to the second number of pump cycles.

The term "pump cycle" as used herein is intended to refer to one complete operation of the pumps, for example, wherein the first pump receives dialysate from a source of dialysate and the second pump expels dialysate to a drain, followed by the first pump expelling dialysate into the dialyser and the second pump removing dialysate from the dialyser.

Accordingly, by operating the device as described in the first aspect of the invention so that the number of pump cycles carried out in a first flow direction is different to the number of pump cycles in the second flow direction, this leads to a net movement of fluid either into or out of the dialyser depending on: whether the first pump chamber or the second pump chamber has the greater volume; and whether or not the first number of pump cycles is greater than or less than the second number of pump cycles. It is typically the case that the difference between the first and second number of pump cycles is equal to one. It is advantageous to have a small difference between the first and second number of pump cycles as this ensures that neither pump is overly used in the same role (i.e. delivering dialysate to the dialyser or removing dialysate from the dialyser). Over use of one or both of the pumps in a given role could lead to uneven deterioration of the pump systems. For instance, exposing flexible membranes to spent dialysate more than fresh dialysate may lead to faster degradation of the membrane due to the presence of certain corrosive impurities present in the spent dialysate but not present in fresh dialysate.

There is also provided in a fourth aspect of the invention a method of operating the dialysis machine according to the second aspect of the invention comprising the steps of; delivering fresh dialysate solution to the dialyser; and removing spent dialysate solution from the dialyser; characterised in that the volume flow rate of at least one of the pumps is varied so that the volumes of dialysate pumped by the first and second pumps are different for at least one pump cycle in order to remove excess fluid from the dialyser and/or deliver excess fluid to the dialyser.

By operating the dialysis machine according to the second aspect of the invention for at least one pump cycle wherein the volume flow rates of the first and second pumps are different, excess fluid can either be delivered to or drawn from the dialyser for each pump cycle wherein the volumes of dialysate pumped by the first and second pumps are different. After the appropriate amount of excess fluid has either been delivered to or removed from the dialyser, the volume rates of the first and second pumps can be restored to being equal and dialysis can be maintained until further ultrafiltration is needed. This is advantageous as it does not require swapping of roles for the first and second pumps and therefore can be used in systems involving less complex valve arrangements. It is typically the case with this method that at least one of the pumps is varied so that the volumes flow rate of the first and second pumps are different for at least one of the pump cycle in order to remove excess fluid from the dialyser.

It is typically the case that the method involves varying the volume of the pump chambers in order to bring about the variation in volume flow rate of least one of the pumps. This can be achieved by, for example, actuating the deployable protrusions present in the base of a pump cavity in order to change the volume of the pump chamber. As such, when the membrane is drawn against the base of the pump cavity the membrane abuts against the protrusions, restricting the volume of the pump chamber.

Alternatively, the frequency of the pumps can be varied typically in situations where the volume of the pump chambers is equal and invariable. Accordingly, the method may involve incorporating an additional pump actuation step for one of the pumps into a pump cycle. The pump cycle may, for instance, where the first pump is responsible for removing spent dialysate from the dialyser, comprise the steps of: actuating the first pump to remove dialysate from the dialyser and actuating the second pump to deliver fresh dialysate to the dialyser, actuating the first pump to expel spent dialysate to the drain, actuating first pump again to remove further fluid from the dialyser, and actuating the first pump again to expel said further fluid to the drain and actuating the second pump to drawn fresh dialysate into the second pump. In this way, excess fluid is removed from the dialyser equal to the volume of the first pump chamber for this pump cycle.

DESCRIPTION OF THE DRAWINGS

The invention will now be described by way of example only, with reference to the following drawings, in which.

DETAILED DESCRIPTION

Figure 1:
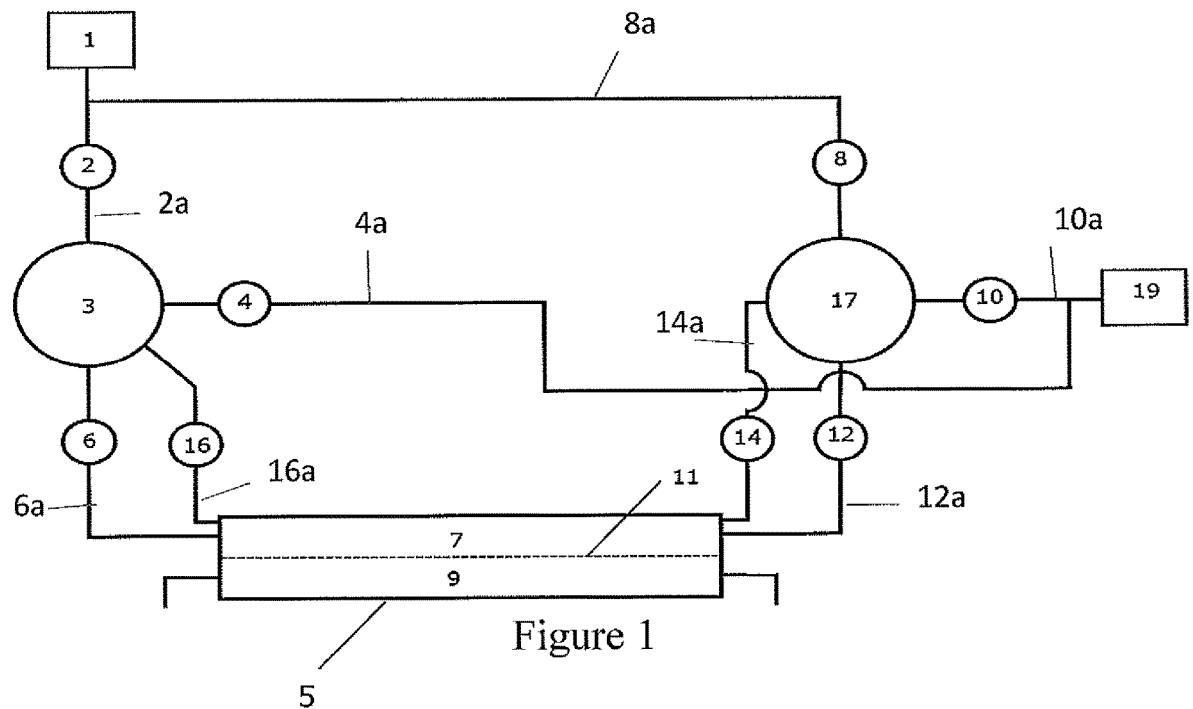
FIG. 1 is a schematic representation of the dialysis machine of the invention.

FIG. 1 shows a typical pumping system for a dialysis machine according to the first aspect of the invention. The system comprises a first pump 3 adapted to receive a fresh dialysate solution from a dialysate source via a first source valve 2 connected via dialysate source line 2a to a source of dialysate 1. The dialysate source line 2a has a first dialysate source valve 2 to control flow of dialysate from the source 1 to the first pump 3. First pump 3 has fluid connections to a dialysate inlet line 6a, dialysate drain line 4a and dialysate outlet line 16a. Dialysate inlet line 6a has dialysate inlet valve 6 thereon. Dialysate drain line 4c has dialysate drain valve 4 thereon. Dialysate outlet line 16a has dialysate outlet valve 16 thereon.

Dialysate inlet line 6a and dialysate outlet line 16a are connected, in fluid communication, to the dialysate side of a dialyser 5 in known manner. Dialysate drain line 4a is connected in fluid communication with a dialysate drain 19. In use, dialysate is drawn into the first pump 3 via the first source valve 2. This first source valve 2 is then closed and the first pump 3 is actuated and the fresh dialysate solution is expelled through the first dialyser inlet valve 6 into the dialyser 5.

The dialyser 5 comprises a first compartment, referred to as the dialysate side 7 and a second compartment referred to as the blood side 9 which are separated from one another by means of a dialyser membrane 11.

The system comprises a second pump 17 which has a mirrored set of fluid lines, connections and valves similar to the pump 3. So, second pump 17 has second dialysate source line 8a with second dialysate source valve 8 connected to dialysate source 1. Second pump also has second dialysate inlet line 14a with second dialysate inlet valve 14, second dialysate outlet line 12a with second dialysate outlet valve 12 and second dialysate drain line 10a with second dialysate drain valve 10.

The second dialysate inlet and outlet lines 14a, 12a are connected to the opposite end of the dialysate side 7 of the dialyser 5. The second dialysate drain line 10a is connected to the dialysate drain 19.

The fresh dialysate solution passes along the dialysate side 7 and impurities in the blood side 9 diffuse across the dialyser membrane 11 into the fresh dialysate solution thereby removing impurities from the blood. This dialysate solution containing impurities leaves the dialyser and is drawn into the second pump 17 via the second dialyser outlet valve 12. The second pump 17 can then be actuated to expel the spent dialysate solution to the drain 19 via the second drain valve 10. The volumes of the first and second pumps (3, 17) are different to one another. The first pump 3 has a smaller volume than the second pump 17. This means that in a single pumping cycle operating in the flow direction described above, excess fluid is drawn from the dialyser and expelled through the drain. In order to counteract this removal of excess fluid the operation of the first pump 3 and the second pump 17 can be switched. Accordingly, after a given number of cycles in the first direction described above, the roles of the first and second pumps 3, 17 can be changed. Accordingly, a fresh dialysate solution can be drawn from the dialysate source 1 into the second pump 17 via the second source valve 8. This fresh dialysate can then be expelled from the second pump 17 via the second dialyser inlet valve 14 and pass into the dialyser 7. Impurities from the blood are transferred via the dialyser membrane 11 into the fresh dialysate as it passes along the dialysate 7 of the dialyser 5. Spent dialysate solution exiting the dialyser 5 enters the first pump 3 via the first dialyser outlet valve 16. This spent dialysate solution can then be expelled from the first pump 3 via the first drain valve 4. Accordingly, where an even number of pump cycles occurs in both directions, there is no net loss of fluid from the system. However, as and when ultrafiltration is required, the number of pump cycles in one of the directions can be made to be greater than or less than the number of pump cycles in the other direction. In the situation where the volume of first pump 3 is less than the volume of the second pump 17, excess fluid can be removed from the dialyser by ensuring that the number of pump cycles in the first direction is greater than the number of pump cycles in the second direction.

Figure 2:
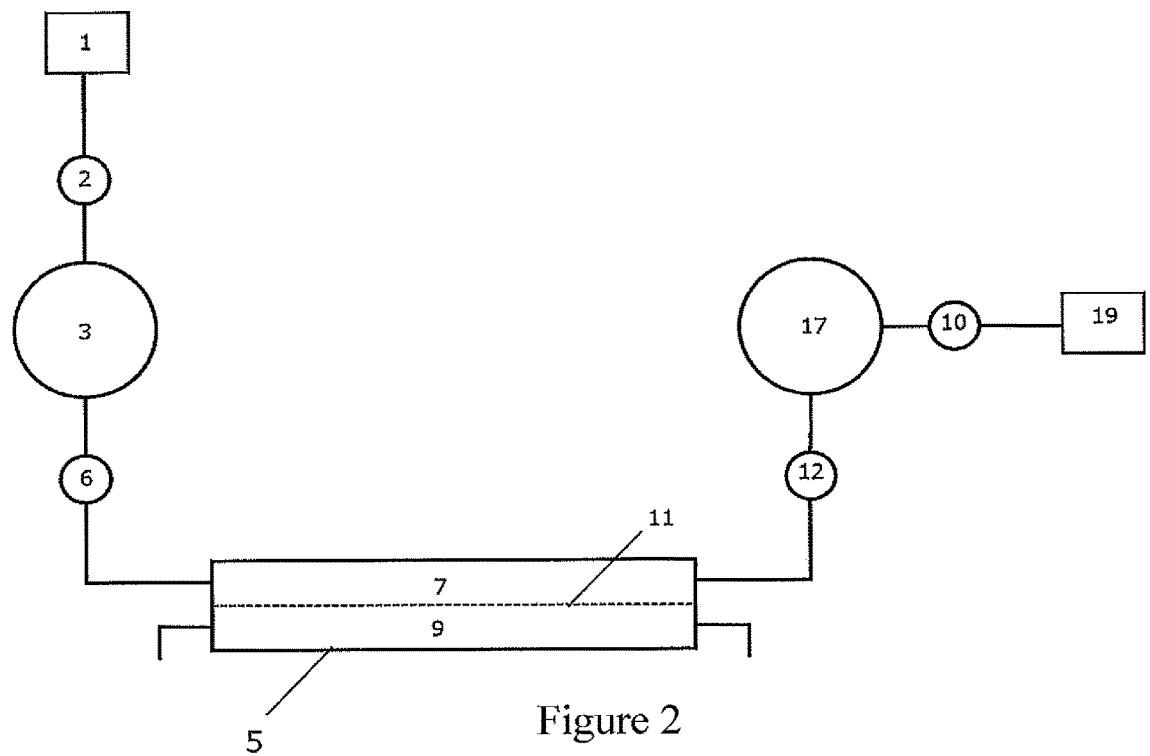
FIG. 2 is a schematic representation an alternative arrangement of the dialysis machine of the invention shown in FIG. 1.

FIG. 2 shows an alternative arrangement according to the second aspect of the invention and the first pump 3 is configured to have a variable volume. In a first configuration, the first pump 3 has a volume equal to that of the second pump 17. Accordingly, in use, dialysate is drawn from a dialysate source 1 via a first source valve 2 into the first pump 3. This fresh dialysate solution is then expelled from the first pump 3 via the first dialyser inlet valve 6 into the dialyser 5. This dialysate solution passes through the dialysate side 7 of the dialyser 5 and impurities in blood present in the blood side 9 of the dialyser 5 pass across the dialyser membrane 11 into the dialysate solution. Spent dialysate solution is expelled from the dialyser and enters the second pump 17 via the second dialyser outlet valve 12. This spent dialysate solution is then expelled from the second pump 17 via the second drain valve 10 to the drain 19. In the first configuration, the first and second pumps 3, 17 have the same volume and pumping results in no net loss of fluid from the dialyser. However, as and when ultrafiltration is required, the volume of the first pump 3 can be varied, typically reduced in volume, by deploying protrusions in the base of the pump cavity of the first pump 3. This is shown in more detail in FIG. 3. Accordingly, this reduces the overall volume of the first pump 3. As such, when the above cycle is repeated, the amount of fresh dialysate solution delivered to the dialyser 5 is less than the amount of spent dialysate solution drawn from the dialyser 5 by the second pump 17. Accordingly, this results in a net loss of fluid from the dialyser 5. The operation of the pumps 3,17 can be switched as with the embodiment described above in relation to the first aspect of the invention. However, for ease of clarity only one flow direction has been shown this embodiment.

Figure 3A:
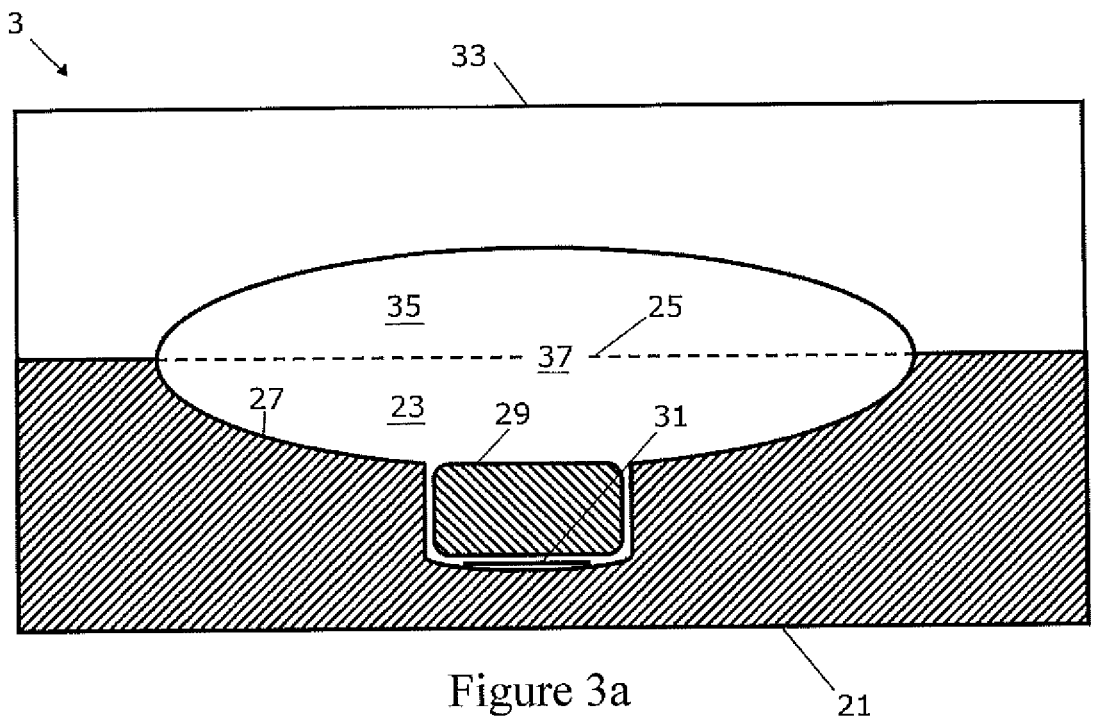
FIG. 3a and FIG. 3b are cross sections through the pump chamber of a membrane pump used in the present invention wherein the pump chamber is empty with protrusions in a deployed and undeployed configuration.
Figure 3B:
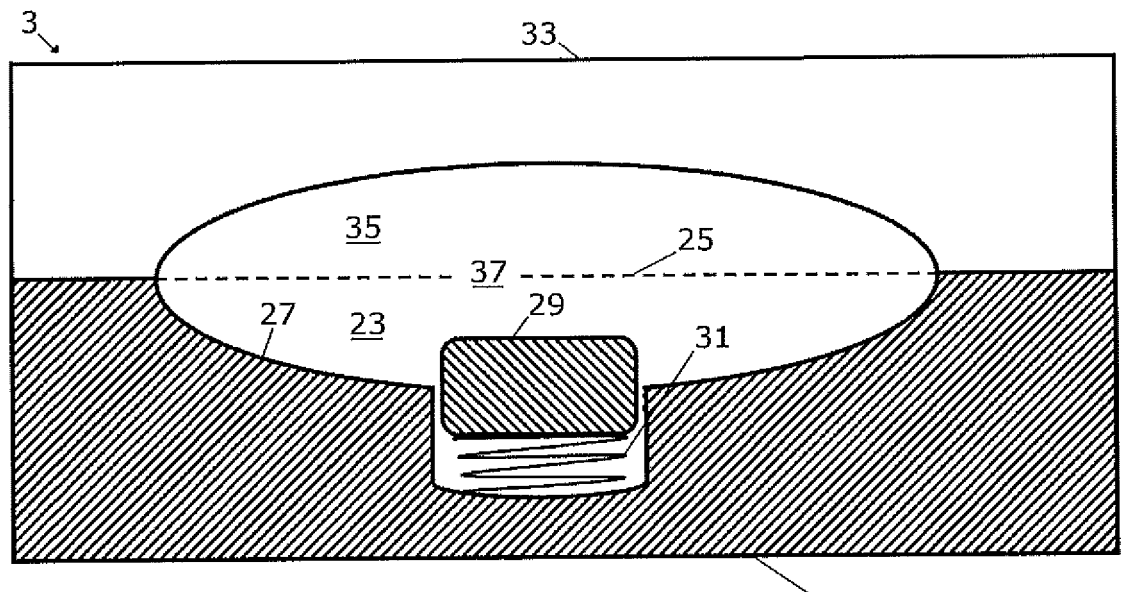

The first and second pumps described herein are membrane pumps which are shown in more detail in FIGS. 3a and 3b.

FIG. 3a shows a cross-section through a pump 3, 17 of the invention. The pump 3, comprises two parts, a dialysis cartridge 33 and a platen 21 on the dialysis machine.

The dialysis cartridge 33 comprises a number of chambers 35 and conduits (not shown) all covered by a flexible membrane 25. The platen 21 includes a pump cavity 23 having a base 27 and a deployable protrusion 29 located within the base of the pump cavity 23 which can be actuated using biasing means 31. The cartridge 33 and the plate 21 together define a pump chamber 37.

The flexible membrane 25 can be manipulated by the dialysis machine through the application of pressure through the platen 21 in order to move the membrane towards and away from the base of pump cavity 27 of the platen 21. This draws fluid through the chambers and conduits of the cartridge 33 and operates membrane valves thereon.

The volume of pump chamber 37 can be varied by moving the deployable protrusions 29 on the platen 21 using the biasing means 31 into the pump cavity 23 thereby reducing the overall volume of the pump chamber 37. The deployed configuration is shown clearly in FIG. 3b. Although the embodiments shown in FIGS. 3a and 3b display a spring as an example of the biasing means 31 that operate the deployable protrusion 29, a range of mechanisms could be employed to actuate the deployable protrusion 29, such as a solenoid or a stepper motor.

Figure 4A:
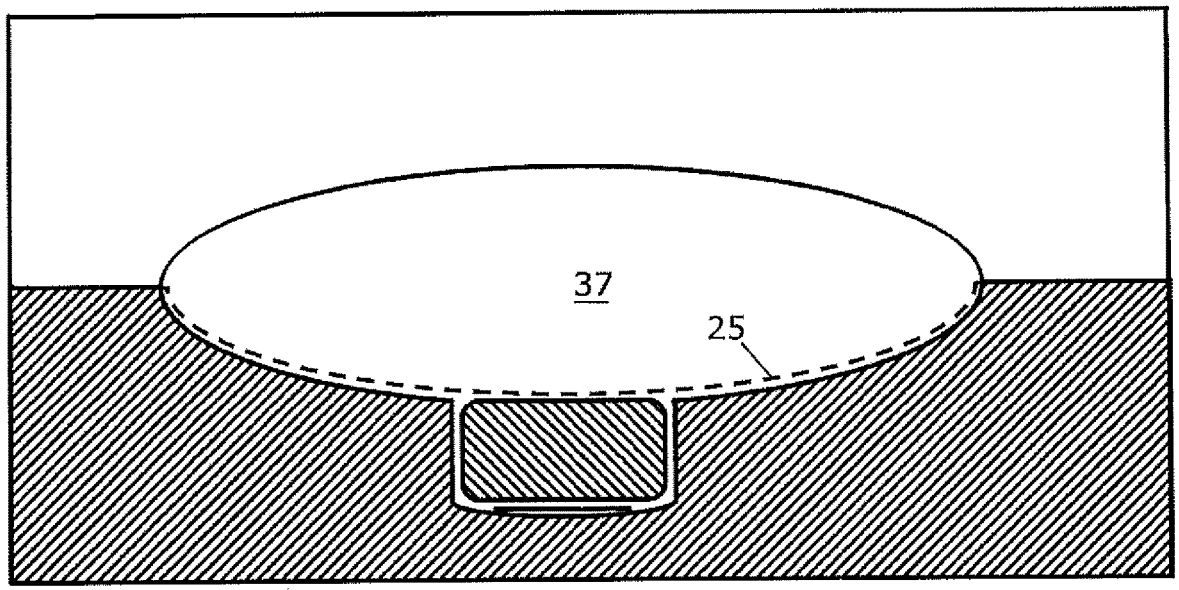
FIG. 4a and FIG. 4b are cross sections through the pump chamber of a membrane pump used in the present invention wherein the pump chamber is full with protrusions in a deployed and undeployed configuration.
Figure 4B:
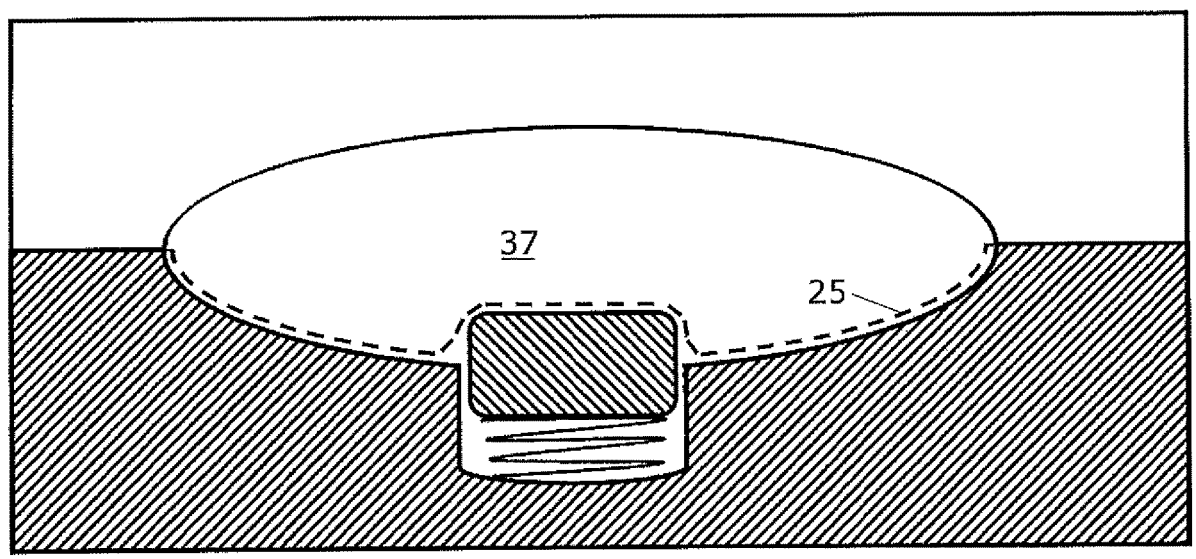

FIGS. 4a and 4b show the pump 3, 17 in both the deployed and undeployed configurations respectively, where the flexible membrane 25 is pulled against the base 27 of the pump cavity 23 in order to draw dialysate into pump chamber. The volume of the pump chamber 37 in FIG. 4b is smaller than that in FIG. 4a as deployable protrusion 29 is in the deployed configuration and so effectively reduces the overall volume of pump chamber 37.

Figure 5A:
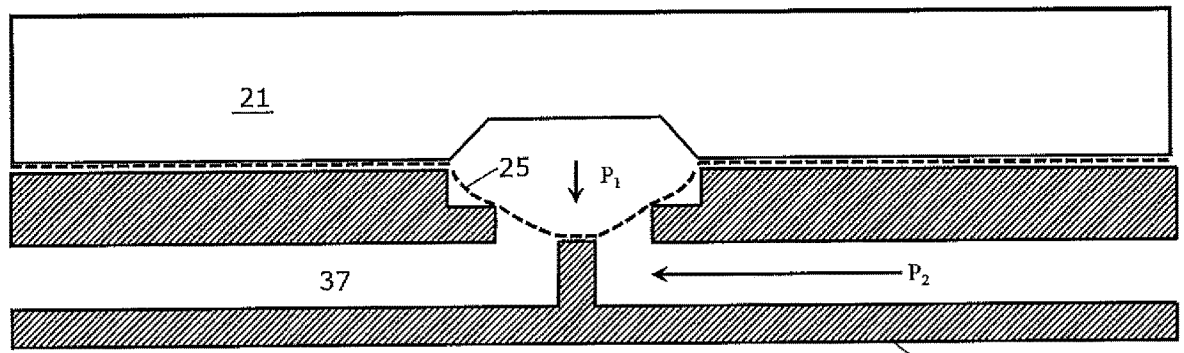
FIG. 5a and FIG. 5b are cross sections of a membrane valve used in the present invention wherein the valve closure positions are variable.
Figure 5B:
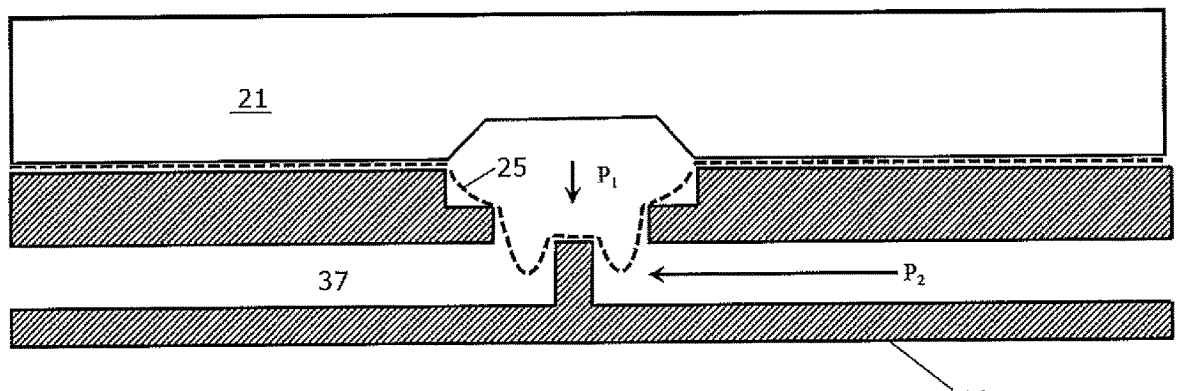

FIGS. 5a and 5b show cross-sections through one of the valves used in the dialysis cartridge 33 suitable for use with a device of the claimed invention. The valve 41 consists of a channel 37 with an opening covered by a flexible membrane 25. When pressure is applied to the flexible membrane 25 the membrane 25 is forced down into the valve opening so as to seal the channel 37. Because the membrane 35 is flexible, the ratio between pressure $P_1$ and $P_2$ applied to the flexible membrane changes the volume of the valve cavity 39. FIG. 5A shows a situation where $P_1$ is slightly greater than $P_2$ whilst FIG. 5b shows a situation where $P_1$ is much greater than $P_2$. This has the effect of forcing membrane 25 further into the valve openings, changing the shape of the membrane valve closure position which changes the volume of the valve cavity.

By varying the valve cavity volume in this way, the pump volume can be altered so as to control the volume flow rate of the pump.

The invention claimed is:

1. A dialysis machine for ultrafiltration, co p sing:
a dialyser; and
a first pump and a second pump,
wherein:
each pump is adapted to deliver a fresh dialysate solution to the dialyser and remove a spent dialysate solution from the dialyser,
at least one of the first and second pumps comprising a cartridge and a platen,
the cartridge comprising a plurality of chambers and conduits covered by a flexible membrane,
the platen and cartridge further defining a membrane valve comprising a channel with an opening covered by the flexible membrane a valve cavity;
a volume flow rate of the first pump is different from a volume flow rate of the second pump; and
operation of at least one of the first pump and the second pump is configured to at least one of:
remove excess fluid from the dialyser and deliver excess fluid to the dialyser,
the dialysis machine being configured to vary the volume of the valve cavity by controlling the pressure differential across the flexible membrane of the membrane valve in order to change the shape of the flexible membrane when the membrane valve is in a closed configuration so as to effect at least one of the removal of excess fluid from the dialyser and delivery of excess fluid to the dialyser.

2. A dialysis machine for ultrafiltration comprising:
a dialyser;
a first pump adapted to deliver a fresh dialysate solution to the dialyser; and
a second pump adapted to remove a spent dialysate solution from the dialyser;
wherein
at least one of the first and second pumps comprising a cartridge and a platen,
the cartridge comprising a plurality of chambers and conduits covered by a flexible membrane,
the platen and cartridge defining a membrane valve comprising a valve cavity and a channel with an opening covered by the flexible membrane;
a volume flow rate of at least one of the first pump and the second pump is variable;
the volume flow rate of at least one of the first pump and the second pump are configured to at least one of remove excess fluid from the dialyser and deliver excess fluid to the dialyser;
and
the dialyser being configured to vary the volume of the valve cavity, by controlling the pressure differential across the flexible membrane of the membrane valve in order to change the shape of the flexible membrane when the membrane valve is in a closed configuration.

3. A dialysis machine according to claim 2, wherein the volume of at least one of the pumps is variable.

4. The dialysis machine of claim 3, wherein the volume of the first pump and the volume of the second pump are variable.

5. The dialysis machine of claim 4, wherein the volume of the first pump is different from the volume of the second pump.

6. The dialysis machine of claim 5, wherein the first pump and the second pump are operated at a different frequency.

7. The dialysis machine of claim 6, wherein an operation of the first pump and/or the second pump is configured to remove excess fluid from the dialyser.

8. The dialysis machine of claim 7, wherein the dialysis machine does not comprise a separate ultrafiltration pump.

9. The dialysis machine of claim 8, wherein the first pump and/or the second pump are flow balance pumps.

10. The dialysis machine of claim 9, wherein the first pump and/or the second pump comprise a pump chamber, a volume of the pump chamber of at least one of the first pump and/or the second pump is variable.

11. The dialysis machine of claim 10, wherein the pump cavity comprises a base including one or more deployable protrusions.

12. The dialysis machine of claim 11; wherein a difference between the volume flow rate of the first pump and the volume flow rate of the second pump is at least 1%.

13. The dialysis machine of claim 12, wherein a difference between the volume flow rate of the first pump and the volume flow rate of the second pump ranges from about to about 50%.

14. A method of operating the dialysis machine for ultrafiltration comprising:
   providing a dialysis machine comprising a dialyser, a first pump, and a second pump, wherein:
      a volume flow rate of the first pump is different from a volume flow rate of the second pump;
      the first pump and the second pump each comprising a cartridge and a platen,
      the cartridge comprising a plurality of chambers and conduits covered by a flexible membrane,
      the platen and cartridge further defining a membrane valve comprising a channel with an opening covered by the flexible membrane a valve cavity; and
      an operation of at least one of the first pump and the second pump is configured to remove excess fluid from the dialyser and/or deliver excess fluid to the dialyser,
   for at least one of the first pump and the second pump, varying the volume of the valve cavity by controlling a pressure differential across the flexible membrane of the membrane valve in order to change the shape of the flexible membrane when the membrane valve is in a closed configuration in order to effect the removal of excess fluid from the dialyser and/or delivery of excess fluid to the dialyser.

15. A method of operating a dialysis machine for ultrafiltration comprising:
   providing a dialysis machine comprising a dialyser, a first pump adapted to deliver a fresh dialysate solution to the dialyser, and a second pump adapted to remove a spent dialysate solution from the dialyser;
   wherein:
      at least one of the first and second pumps comprising a cartridge and a platen,
      the cartridge comprising a plurality of chambers and conduits covered by a flexible membrane,
      the platen and cartridge defining a membrane valve comprising a valve cavity and a channel with an opening covered by the flexible membrane;
      a volume flow rate of at least one of the first pump and the second pump:
      is variable; and
      configured to at least one of remove excess fluid from the dialyser and deliver excess fluid to the dialyser;
   and
   for at least one of the first pump and the second pump; varying the volume of the valve cavity by controlling a pressure differential across the flexible membrane of the membrane valve in order to change the shape of the flexible membrane when the membrane valve is in a closed configuration.

* * * * *